(12) United States Patent
Shuman et al.

(10) Patent No.: US 10,092,343 B2
(45) Date of Patent: Oct. 9, 2018

(54) MECHANICALLY HEATED CATHETER

(71) Applicant: Spiration, Inc., Redmond, WA (US)

(72) Inventors: Brandon J. Shuman, Kirkland, WA (US); Clint Finger, Bellevue, WA (US)

(73) Assignee: Spiration Inc., Redmond, WA (US)

( * ) Notice: Subject to any disclaimer, the term of this patent is extended or adjusted under 35 U.S.C. 154(b) by 404 days.

(21) Appl. No.: 14/198,888

(22) Filed: Mar. 6, 2014

(65) Prior Publication Data

US 2014/0276715 A1 Sep. 18, 2014

Related U.S. Application Data

(60) Provisional application No. 61/788,773, filed on Mar. 15, 2013.

(51) Int. Cl.
*A61B 18/04* (2006.01)
*A61B 18/08* (2006.01)
*A61B 18/00* (2006.01)

(52) U.S. Cl.
CPC ............ *A61B 18/082* (2013.01); *A61B 18/08* (2013.01); *A61B 2018/0019* (2013.01); *A61B 2018/00095* (2013.01); *A61B 2018/00184* (2013.01); *A61B 2018/00196* (2013.01); *A61B 2018/00202* (2013.01); *A61B 2018/00541* (2013.01)

(58) Field of Classification Search
CPC ..................................................... A61B 18/08
See application file for complete search history.

(56) References Cited

U.S. PATENT DOCUMENTS

| 6,123,084 | A  | * | 9/2000 | Jandak   | A61B 18/08 128/898 |
| 6,355,030 | B1 | * | 3/2002 | Aldrich  | A61B 18/08 606/28 |
| 8,465,486 | B2 |   | 6/2013 | Danek et al. | |
| 2003/0023239 | A1 | * | 1/2003 | Burbank | A61B 10/0275 606/45 |

(Continued)

OTHER PUBLICATIONS

"Friction and Coefficients of Friction." The Engineering Toolbox. http://www.engineeringtoolbox.com/friction-coefficients-d_778.html <Retrieved Apr. 26, 2016.>.*

(Continued)

*Primary Examiner* — Luther G Behringer

(57) ABSTRACT

Systems and methods for mechanically heated catheter tips are provided. The systems include, for example: a catheter body with an axial lumen; a catheter tip with at least some of the tip constructed out of a high-friction, thermally-conductive material; a friction producing plug disposed in the axial lumen of the catheter tip and constructed at least in part out of a high-friction material; a drive wire running through the axial lumen of the catheter body being connected on the proximal end to a power source and on the distal end to the friction producing plug. Methods include using the drive wire to rotationally or axially translationally move the friction producing plug within the catheter tip. The friction produced by the movement of the friction producing plug and the inner wall of the catheter tip generates heat which can be conducted outward by the thermally conductive material.

11 Claims, 6 Drawing Sheets

(56) References Cited

U.S. PATENT DOCUMENTS

2010/0249601 A1* 9/2010 Courtney ............. A61B 5/0066
600/463
2013/0253623 A1 9/2013 Danek et al.
2013/0261368 A1 10/2013 Schwartz

OTHER PUBLICATIONS

Translation of Office Action from China Patent Office, dated Jan. 23, 2017.
Translation of Decision of Rejection at JPO, dated Mar. 6, 2017.

* cited by examiner

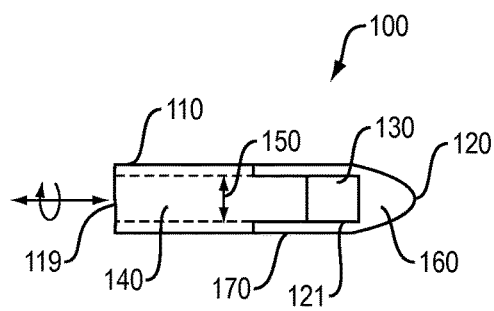
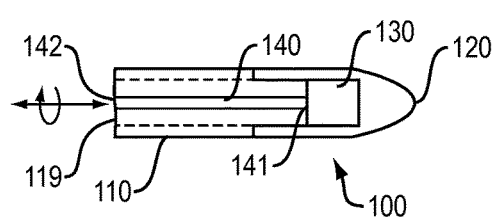
FIG. 1A
FIG. 1B
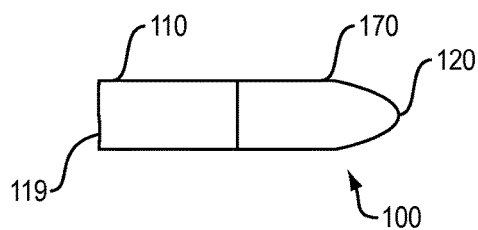
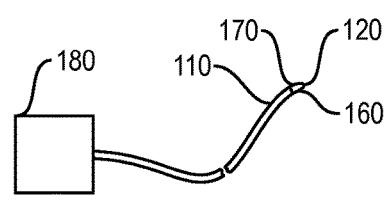
FIG. 1C
FIG. 1D

MECHANICALLY HEATED CATHETER

CROSS REFERENCE TO RELATED APPLICATIONS

This application claims priority to and the benefit of U.S. provisional patent application Ser. No. 61/788,773 filed on Mar. 15, 2013 entitled "Mechanically Heated Catheter," the entire disclosure of which is hereby incorporated by reference as if set forth in its entirety for all purposes.

TECHNICAL FIELD

The present invention relates to devices, systems and methods for heat production and delivery catheters. More specifically, the present disclosure relates to devices, systems and methods for mechanically-generated heat delivery and delivery catheters

BACKGROUND

Description of the Related Art

The application of heat (e.g., localized hyperthermia, thermal ablation, thermal coagulation, or thermal cautery) to the human body is a common therapy and has many clinical applications. Some representative applications of heat include, but are not limited to destruction of cancerous tissues, destruction or mitigation of infection, and modification of aberrant cells (e.g., asthma therapy). Currently used methods for the clinical application of heat to tissues entail heat generation by employing electrical energy (e.g., radiofrequency ablation), radiative energy (e.g., laser ablation), and/or acoustic energy (e.g., high intensity focused ultrasound).

The aforementioned methods have several limitations, including, in some applications, the shared shortcoming of large generator size. Large generators are undesirable because they tend to be cumbersome to transport from bedside to bedside. Furthermore, such generators are frequently expensive, thereby increasing the costs of patient care. For example, electrical energy requires a high frequency generator; radiation energy requires a microwave generator or laser pump; and acoustic energy requires an ultrasonic transducer. Moreover, many currently used methods of heat generation for clinical applications necessitate the use of electricity for proper operation and may suffer from poor control over the thermal temperature rise in the tissue itself. Furthermore, it may be undesirable to pass electric currents through the body.

Accordingly, there is a need for improved devices, systems and methods for creating mechanically-based heat generation for tissue treatment and clinical applications.

SUMMARY

In accordance with one embodiment, a catheter to deliver heat is provided. The system can comprise a catheter body, a hollow catheter tip, a friction producing plug, a drive wire, and a power source. The catheter body can comprise an axial lumen. In some embodiments, the hollow catheter tip is configured to attach to one end of the axial lumen of the catheter body and is constructed, at least partially, from a high friction material. The friction producing plug can be configured to fit inside the hollow catheter tip and is constructed, at least partially, from a high friction material. The drive wire extends through the entire length of the axial lumen of the catheter body and into the hollow catheter tip where it is configured to attach to the friction producing plug disposed within the hollow catheter tip. The power source is configured to attach to one end of the drive wire and provide either rotational or axial translational movement to the drive wire.

Accordingly, pursuant to one aspect of the present invention, there is contemplated that apparatus, a catheter to deliver heat, comprising a catheter body comprising an axial lumen having a length extending from a proximal end to a distal end; a hollow catheter tip, where the hollow catheter tip is operably connected to the distal end of the axial lumen of the catheter body, and wherein at least a portion of the hollow catheter tip is constructed from a material with a coefficient of friction of 0.2 to 0.8 high friction material; a friction producing plug, wherein the friction producing plug is configured to fit inside the hollow catheter tip, and wherein at least a portion of the friction producing tip is constructed from a material with a coefficient of friction of 0.2 to 0.8 high friction material; a drive wire having a proximal end and a distal end and extending through the length of axial lumen of the catheter body into the hollow catheter, and wherein the distal end of the drive wire is configured to attach to the friction producing plug; and a power source, wherein the power source is configured to attach to the proximal end of the drive wire, and where the hollow catheter tip contains thermally conductive material.

The invention may be further characterized by one or any combination of the features described herein, such as the power source is configured to provide rotational movement to the drive wire; the power source is configured to provide axial translational movement to the drive wire; movement of the drive wire is modulated using a power input selected from the group including: electric motors, ultrasonic horns, piezoelectric devices, mechanical air driven devices, harmonic devices, air driven pistons, solenoids, and electromagnet drivers; wherein the drive wire, the catheter body, or both, are constructed out of a low friction material; the drive wire, the catheter body, or both, are coated in a low friction material; a inner cavity of the catheter body is filled with oil; the hollow catheter tip is constructed out of at least one material selected from the group including: stainless steel, titanium, and nitinol; the friction producing plug is constructed out of at least one material selected from the group including: ceramic, copper, steel, minerals, cellulose, aramid, chopped glass, rubber and brass, and polyether ether ketone; the friction producing plug is formed monolithically out of a single material; the friction producing plug is formed in a shape selected from the group including: spherical, cylindrical, and bullet shaped; the catheter body comprises a plug stop; a shape of the plug stop is selected from a group consisting of continuous flange-style and bullet shaped; the catheter tip is coated in thermally insulating material and a heat conductive gel is placed in a treatment region before a treatment is applied; the catheter is configured to provide heat inside a human patient.

Pursuant to yet another aspect of the present invention, there is contemplated a method, comprising providing heat inside a human patient using a catheter, comprising providing power to a drive wire, the drive wire having a proximal end and a distal end and extending through the length of an axial lumen of a catheter body, and the distal end of the drive wire is configured to attach to a friction producing plug; the power source is connected to a proximal end of the drive wire; rotationally or axially moving the friction producing plug contained within an axial lumen of a catheter tip which is connected to the drive wire; and dissipating heat from the friction produced by the movement of the friction producing plug outward into a human body through thermally conductive material.

BRIEF DESCRIPTION OF THE DRAWINGS

The foregoing and other features, aspects and advantages of the present disclosure are described in detail below with reference to the drawings of various embodiments, which are intended to illustrate and not to limit the disclosure. The drawings comprise the following figures in which:

FIG. 1A illustrates a longitudinal section view of one embodiment of a catheter with a mechanically heated catheter tip.

FIG. 1B illustrates a longitudinal section view of a second embodiment of a catheter with a mechanically heated catheter tip.

FIG. 1C illustrates an external view of one embodiment of a catheter with a mechanically heated catheter tip.

FIG. 1D illustrates a schematic view of one embodiment of a system for heat generation using a catheter with a mechanically heated catheter tip.

DETAILED DESCRIPTION

Figure 2A:
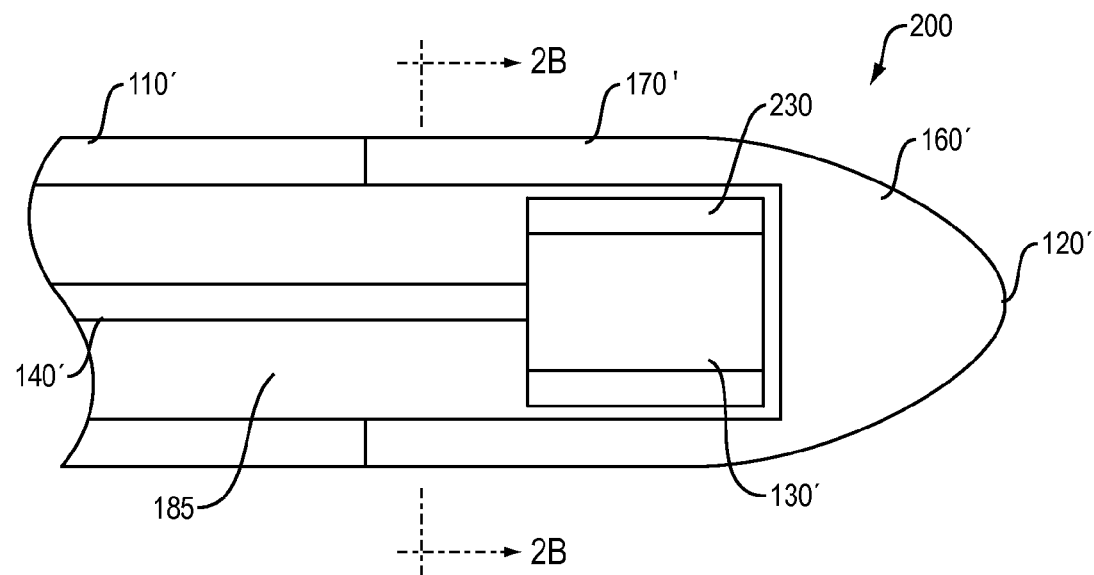
FIG. 2A illustrates a longitudinal section view of another embodiment of a catheter with a mechanically heated catheter tip.

Catheters capable of applying or directing heat in the human body may be used in any of a number of clinical applications as mentioned above. The devices, systems, and methods described herein are not intended to limit the scope of this disclosure. Rather, it will be apparent to one of skill in the art that the devices, systems, and methods disclosed herein can be used in many clinical applications, including, but not limited to cancer therapies (e.g., carcinoma ablation, hyperthermia, thermal ablation, etc.), mitigation of infection, and asthma therapies (e.g., modification or destruction of aberrant cells), etc. For example, such a mechanically heated catheter can be passed down a bronchoscope to treat a patient (e.g., asthma therapies, or possibly pulmonary tumors) using thermal energy generated by friction.

FIG. 1 illustrates a catheter with a mechanically heated catheter tip 100 (e.g., distal end of the catheter). FIGS. 1A & 1B illustrate cross sections of the mechanically heated catheter tip 100. FIG. 1C illustrates an external view of the mechanically heated catheter tip 100. The mechanically heated catheter tip 100 can include a catheter body 110, an axial lumen 121 having a length extending from a proximal end 119 to a distal end, a catheter tip distal end 120, a friction producing plug 130, a drive wire 140, a drive wire diameter 150, a catheter high friction material 160, and a thermally conductive catheter tip 170. It is contemplated that the high friction material may be a material with a coefficient of friction of 0.2 to 0.8, or more preferably a material with a coefficient of friction of 0.4 to 0.7.

In operation, the friction producing plug 130, which can be in substantially uniform contact with the inside of the thermally conductive catheter tip 170 (and therefore the catheter high friction material 160) can be moved by the drive wire 140. The movement of the friction producing plug 130 can be either rotational about the axis of the catheter body 110, or it may be axial along the longitudinal axis of the catheter body 110. In further operation, the movement of the friction producing plug 130 across the inner surface of the thermally conductive catheter tip 170, which can be composed of catheter high friction material 160, generates friction. With sufficient power provided by the drive wire 140 and time, the friction produced upon the movement of the friction producing plug 130 generates heat. The power of the drive wire 140 can be converted by the interaction of the surface of the friction producing plug 130 and the inner wall of the thermally conductive catheter tip 170 (e.g., the catheter high friction material 160) into thermal energy. The thermal energy generated by the drive wire 140 and catheter high friction material 160 can heat the catheter high friction material 160, and consequently the thermally conductive catheter tip 170, which may therefore be used for therapeutic applications of heat. In yet further operation, the magnitude of thermal energy generated by the catheter with a mechanically heated catheter tip 100 can be modulated by a user by increasing or decreasing the power applied through the drive wire 140 (e.g., a user may decrease the drive wire's 140 rotational speed or may increase the speed at which the drive wire 140 oscillates axially).

In some embodiments, the catheter with a mechanically heated catheter tip 100 can have an external diameter (e.g., the external diameter of the catheter body 110 and thermally conductive catheter tip 170) in the range of about 3-35 French, preferably about 7-31 French, and more preferably about 17-21 French, including about 19 French or any other diameter which will allow the construction and operation of to catheter with a mechanically heated catheter tip 100. In some embodiments, the anastomosis of the catheter body 110 and the thermally conductive catheter tip 170 is substantially flush, thereby advantageously facilitating passage of the catheter 100 through the target vessel(s).

In some embodiments, the drive wire diameter 150 can be large (e.g., substantially equivalent to the diameter of the friction producing plug 130 (and therefore substantially equivalent to the inner diameter of the thermally conductive catheter tip 170)). In these embodiments, the drive wire 140 and/or the catheter body 110 can be constructed out of a low friction material to advantageously reduce energy and power loss along the length of the drive wire 140 and allow the maximum delivery of energy to the friction producing plug 130 and the maximum amount of thermal energy generation. In other embodiments, rather than being constructed of one homogeneous material, the exterior surface of the drive wire 140 and/or the interior surface of the catheter body 110 may be coated in a low friction material to advantageously reduce energy and power loss along the length of the drive wire 140 and allow the maximum delivery of energy to the friction producing plug 130 and the maximum amount of heat generation. Representative examples, not meant to limit the scope of this disclosure, of low friction materials which may be used to construct a large diameter drive wire 140 and/or catheter body 110 include: stainless steel, nitinol, titanium, polytetrafluoroethylene, ceramics, FEP, high density polyethylene, and oil impregnated materials. Representative examples, not meant to limit the scope of this disclosure, of low friction materials which may be used to coat a large diameter drive wire 140 and/internal surface of a catheter body 110 include: polytetrafluoroethylene, expanded polytetrafluoroethylene, ceramic coatings, FEP, high density polyethylene, and oil impregnated metals. In some embodiments, the inner cavity of the catheter body 110 surrounding the drive wire 140 can be filled with an oil to advantageously decrease friction between the catheter wall and the drive wire 140. In some embodiments, the drive wire diameter 150 can be small (e.g., substantially smaller than the diameter of the friction producing plug 130). In some embodiments, the material out of which the drive wire 140 is constructed can be given more latitude than when the drive wire diameter 150 is substantially equivalent to the diameter of the friction producing plug 130. For example, there can be less interaction between the outer surface of the drive wire 140 and the inner surface of the catheter body 110. However, even in these embodiments, low friction materials may be advantageously used. Some representative examples of materials which can be used to construct a small diameter drive wire 140, not meant to limit the scope of this disclosure, include: stainless steel, nitinol, and titanium. Some representative examples of low friction materials which can be used to construct a small diameter drive wire 140, not meant to limit the scope of this disclosure, include: polymeric materials (e.g., high density polyethylene, polytetrafluoroethylene, polyamides (i.e., nylon)), and composite materials. As disclosed with respect to a large diameter catheter body 110, in some embodiments, the exterior surface of the small diameter drive wire 140 and/or the interior surface of the catheter body 110 may be coated in a low friction material to advantageously reduce energy and power loss along the length of the drive wire 140 and allow the maximum delivery of energy to the friction producing plug 130 and the maximum amount of heat generation. Representative examples, not meant to limit the scope of this disclosure, of low friction materials which may be used to coat a small diameter drive wire 140 and/internal surface of a catheter body 110 include: polytetrafluoroethylene, expanded polytetrafluoroethylene, ceramic coatings, FEP, high density polyethylene, and oil impregnated metals. In some embodiments, the inner cavity of the catheter body 110 surrounding the small diameter drive wire 140 (i.e. hollow catheter tip 185) can be filled with an oil to advantageously decrease friction between the catheter wall and the drive wire 140.

In some embodiments, the friction producing plug 130 has a diameter that is substantially equivalent to the inner diameter of the thermally conductive catheter tip 170. In some embodiments, the friction producing plug 130 may be translated axially (e.g., along the axis of the catheter with a mechanically heated catheter tip 100) or rotate (e.g., about the axis of the catheter with a mechanically heated catheter tip 100) without being too tight which can cause binding or being too loose which can cause wobbling. In some embodiments, the friction producing plug 130 can be cylindrical and homogeneous (e.g., formed monolithically out of a single material), as shown in FIG. 1. In some embodiments, the monolithic friction producing plug 130 is formed out of a high friction material, including but not limited to: ceramic, copper, steel, minerals, cellulose, aramid, chopped glass, rubber and brass, polyether ether ketone (i.e., PEEK) or any other high friction material.

In some embodiments, the drive wire 140 can be attached to the friction producing plug 130 by any of a number of mechanisms, including threads, adhesive, welding, soldering, expansion clips, grommets, rivets, etc. In other embodiments, the drive wire 140 can be attached to the friction producing plug 130 by any mechanism allowing either axial translation or rotation of the friction producing plug 130 and drive wire 140. In embodiments in which rotation of the friction producing plug 130 is used, the connection between the drive wire 140 and friction producing plug 130 can be of sufficient strength to withstand the torque necessary to generate friction between the friction producing plug 130 and catheter high friction material 160.

In some embodiments, the thermally conductive catheter tip 170, which can have an internal lumen to accommodate the friction producing plug 130, is constructed out of a single material, including but not limited to stainless steel, titanium, nitinol, or any other biocompatible thermally conductive material capable of interacting with the surface of the friction producing plug 130 to generate thermal energy. In some embodiments, the thermally conductive catheter tip 170 is constructed out of two or more layers, including at least an inner friction producing layer, and an outer, biocompatible thermally conductive layer. For example, the inner friction producing layer can be constructed out of a material not necessarily biocompatible (e.g., ceramic, copper, steel, minerals, cellulose, aramid, chopped glass, rubber and brass, or any other high friction material) while the outer layer can be constructed out of a material that is both biocompatible and thermally conductive (e.g., stainless steel). Therefore, the friction producing plug 130 can interact with the inner friction producing layer to optimally generate thermal energy which the outer biocompatible thermally conductive layer can conduct the thermal energy to the target site. In this manner, thermal energy can be delivered to a site while advantageously using bio-incompatible materials optimal for generating the desired thermal energy.

In some embodiments, the thermally conductive catheter tip 170 includes a catheter tip distal end 120 which is substantially bullet-shaped (as illustrated in FIG. 1) to advantageously facilitate navigation through corporeal lumens (e.g., blood vessels). In some embodiments, the thermally conductive catheter tip 170 can taper from a cylinder where the thermally conductive catheter tip 170 meets the catheter body 110 to a rounded tip at the catheter tip distal end 120 (as shown in FIG. 1C). In some embodiments, the thermally conductive catheter tip 170 can have any shape desired.

In some embodiments, the thermally conductive catheter tip 170 is removable from the catheter body 110 by the use of a mechanism such as, but not limited to, threads and clips. In some embodiments, the thermally conductive catheter tip 170 may be constructed so as to be sterilizable and therefore re-usable. In some embodiments, the thermally conductive catheter tip 170 is permanently fixed to the catheter body 110. In such embodiments, the catheter with a mechanically heated catheter tip 100 may be constructed so as to be sterilizable and therefore re-usable. In some embodiments, the catheter with a mechanically heated catheter tip 100 can be constructed so as to be appropriate for only a single use, and therefore be disposable.

The distal end of the catheter body 110 is anastomosed to the proximal end of the thermally conductive catheter tip 170 as disclosed above. The catheter body 110 extends proximally for a distance which can be in the range of about 50-3000 cm, preferably about 200-2250 cm, and more preferably about 500-750 cm, including about 600 cm or any other length needed to reach the target site. The drive wire 140 exits the proximal end of the catheter body 110 where the drive wire 140 is coupled to a power source 180 (as shown in FIG. 1D). The drive wire 140 may have a proximal end 142 and a distal end 141.

In some embodiments, the power source 180 is an oscillator which translates the drive wire 140 back and forth along the axis of the catheter body 110. Translating the drive wire 140 along the axis of the catheter body 110 can translate the friction producing plug 130 along the catheter high friction material 160 of the internal lumen of the thermally conductive catheter tip 170 thereby generating friction-induced thermal energy. In embodiments in which the power source 180 is an oscillator, the power source 180 can be any of the mechanisms including, but not limited to, electric motors, ultrasonic horns, piezoelectric devices, mechanical air driven devices, harmonic, devices, air driven pistons, solenoids, or electromagnet drivers, or any other mechanism capable of rapidly oscillating the drive wire 140. As an illustrative example, compressed air can be used to drive a mini turbine which can oscillate the drive wire 140 at high frequencies. In some embodiments, air flowing over a flexible membrane can create a vibration harmonic which can create a translational (e.g., back and forth motion) on the drive wire 140. The amount of heat generated in an embodiment using an oscillating power source 180 can be governed by the following equation, where P is the power generated or dissipated, F is the axial force, d is the distance traveled, and t is the time:

$$P=F*d/t.$$

This equation shows that a high velocity (d/t), set by a high frequency (e.g., in the ultrasonic range) could require very little displacement to generate a large amount of power.

In some embodiments, the power source 180, also referred to as the drive wire power source, is a rotator which rotates the drive wire 140 about the longitudinal axis of the catheter body 110. Rotating the drive wire 140 about the longitudinal axis of the catheter body 110 could therefore rotate the friction producing plug 130 against the catheter high friction material 160 inside the internal lumen of the hollow catheter tip (185) thereby generating friction-induced thermal energy. In some embodiments (e.g., where the drive wire power source 180 is a rotator) the drive wire power source 180 can be any of the mechanisms including, but not limited to, electric motors, ultrasonic horns, piezoelectric devices, mechanical air driven devices, harmonic devices, air driven pistons, or any other mechanism capable of rapidly rotating the drive wire 140. For example, compressed air can be used to drive a mini turbine which can rotate the drive wire 140 at high frequencies. The amount of heat generated (and dissipated to tissue) can follow the following form of the energy and power equation (the energy element of this equation applies to the translation system discussed above), where P is the mechanical power transferred to the tissue (in a rotational system $P=\tau$ (rotational velocity), Q is the heat flux away from the tissue, driven by the thermal conductivity and convection of the tissue surrounding the tissue being heated, M·a is the mass flow rate of the air in the tissue being heated, M·b is the mass flow rate of the blood in the tissue being heated, $C_a$ is the heat capacitance of the air, $C_b$ is the heat capacitance of the blood, $\Delta T_a$ is the change in temperature of the air in the tissue being heated, $\Delta T_b$ is the change in temperature of the blood in the tissue being heated, M is the mass of the tissue being heated, C is the heat capacity of the tissue being heated, and dT/t is the change in temperature of the tissue over time.

$$P-Q+(M\cdot a)C_a\Delta T_a+(M\cdot b)C_b\Delta T_b=MCdT/t$$

In the aforementioned equation and physical situation, the power generated and released at the thermally conductive catheter tip 170 would be in the form of heat and would directly drive the rate of heat transfer through the tissue. The power could be the same for a system using mechanical, electrical, radiative, or acoustic energy. However, there can be a difference in how the power is converted to therapeutic heat. In the system disclosed herein, the power is already in the form of heat, whereas in many other systems, the energy may be required to pass through the resistance of the tissue prior to generate heat (e.g., resistance for electricity, absorption for light, and absorption for sound, etc.).

FIG. 2 illustrates a second catheter with a mechanically heated catheter tip 200. The second catheter tip 200 includes a catheter body 110', a thermally conductive catheter tip 170' constructed out of catheter high friction material 160', a catheter tip distal end 120', a drive wire 140', a friction producing plug 130' and a high friction coating 230. In operation, the second catheter tip 200 can function in a manner similar to the catheter with a mechanically heated catheter tip 100 of FIG. 1.

Figure 2B:
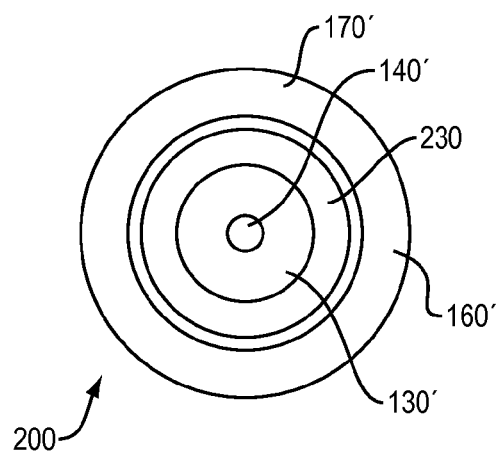
FIG. 2B illustrates a section view perpendicular to the longitudinal axis of the embodiment of a catheter with a mechanically heated catheter tip shown in FIG. 2A.

The friction producing plug 130' of FIG. 2 can be formed out of two or more separate materials. In some embodiments, the inner core is made out of a first material then coated with a high friction coating 230. FIG. 2B shows such a high friction coating 230 coated friction producing plug 130' in cross section view perpendicular to the longitudinal axis of the second catheter tip 200. The high friction coating 230 covering the friction producing plug 130' can interact with the catheter high friction material 160' out of which the thermally conductive catheter tip 170' can be constructed. The use of a high friction coating 230 can allow the use of less high friction material which can advantageously reduce costs, can allow the use of brittle materials (which may not attach well to the drive wire 140'), or can promote better or firmer connection between the friction producing plug 130' and the drive wire 140'.

FIG. 3 illustrates a third catheter with a mechanically heated catheter tip 300. The third catheter tip 300 can include a catheter body 110', a thermally conductive catheter tip 170' constructed out of catheter high friction material 160', a catheter tip distal end 120', a drive wire 140', a cylindrical, spherical or bullet-shaped friction producing plug (i.e., 310, 320, or 330, respectively), and a plug stop 340. In operation, the third catheter tip 300 functions in a manner similar to the catheter with a mechanically heated catheter tip 100 of FIG. 1.

Figure 3A:
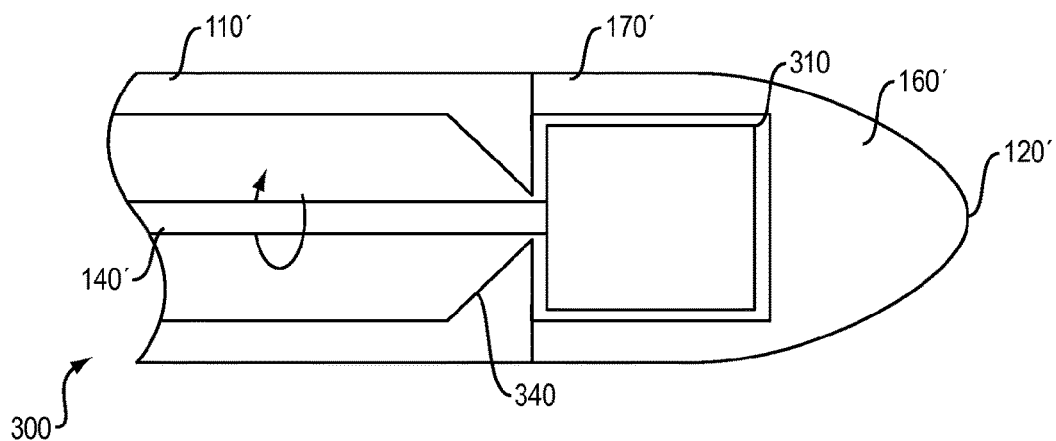
FIG. 3A illustrates a longitudinal section view of one embodiment of a catheter with a mechanically heated catheter tip having a plug stop.

In some embodiments, the friction producing plug may be cylindrical as illustrated by the locked cylindrical friction producing plug 310 of FIG. 3A. In other embodiments, the friction producing plug may be spherical as illustrated by the locked spherical friction producing plug 320 of FIG. 3B. In yet other embodiments, the friction producing plug may be bullet-shaped as illustrated by the locker bullet-shaped friction producing plug 330 of FIG. 3C.

Figure 3B:
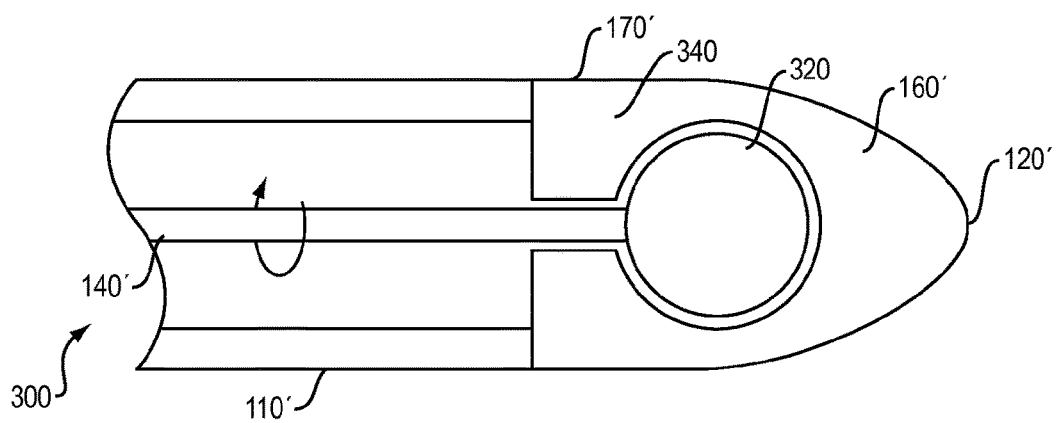
FIG. 3B illustrates a longitudinal section view of another embodiment of a catheter with a mechanically heated catheter tip having a plug stop.
Figure 3C:
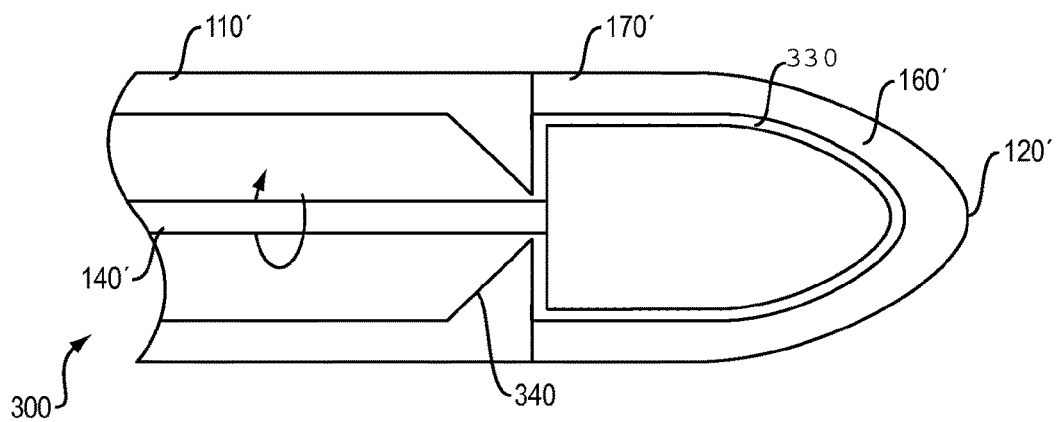
FIG. 3C illustrates a longitudinal section view of another embodiment of a catheter with a mechanically heated catheter tip having a plug stop.

In some embodiments, the plug stop 340 serves to substantially eliminate axial translation of, or "locks", the locked cylindrical friction producing plug 310 of FIG. 3A, the locked spherical friction producing plug 320 of FIG. 3B, and the locked bullet-shaped friction producing plug 330 of FIG. 3C. In some embodiments, the locking plug stop 340 can be combined with rotation of the drive wire 140' about the catheter's longitudinal axis to advantageously reduce or eliminate substantially all axial translation of the friction producing plug, reduce or eliminate substantially all vibration caused by that axial translation, and/or keep the friction producing plug in the proper friction-producing zone within the thermally conductive catheter tip 170', thereby advantageously simplifying operation. In other embodiments, rather than substantially reducing or eliminating axial translation, the plug stop 340 can combine an allowed fixed distance of axial translation with friction plug oscillation along the catheter's longitudinal axis to advantageously keep the friction producing plug in the proper friction-producing zone within the thermally conductive catheter tip 170' thereby advantageously simplifying operation. The plug stop 340 can be any structure capable of restricting axial translation of the friction producing plug, such as the continuous flange-style plug stop 340 illustrated in FIG. 3A, FIG. 3B, and FIG. C.

Figure 4A:
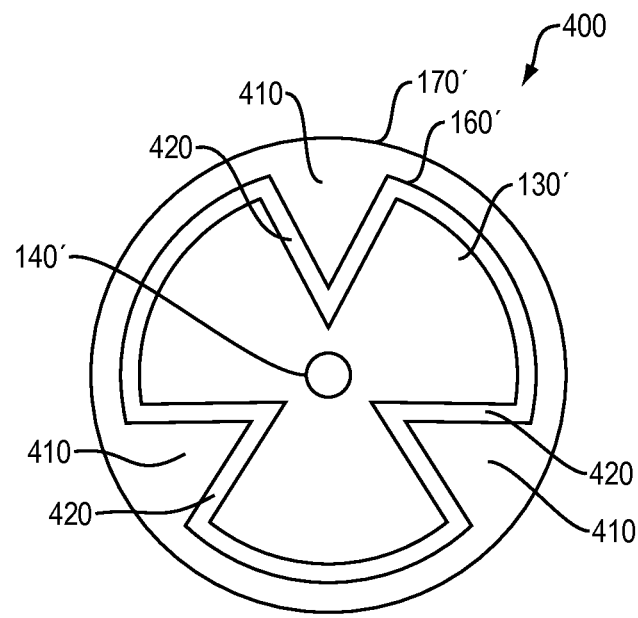
FIG. 4A illustrates a section view perpendicular to the longitudinal axis of a catheter with a mechanically heated catheter tip having a grooved friction producing plug.
Figure 4B:
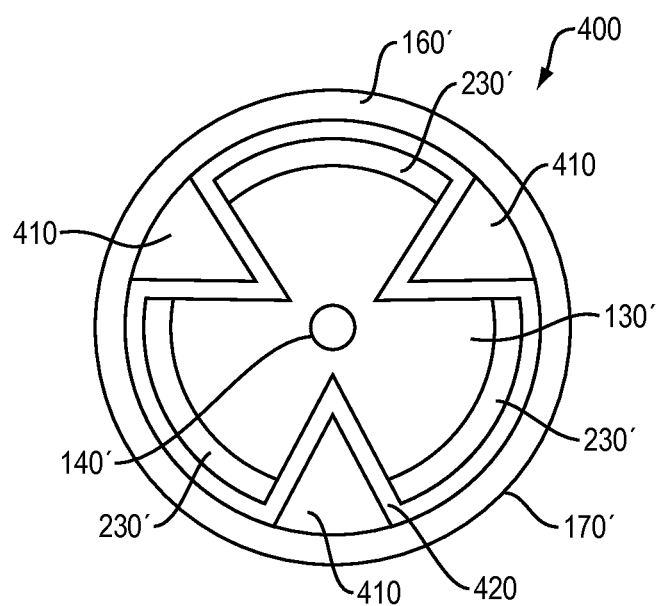
FIG. 4B illustrates a section view perpendicular to the longitudinal axis of another catheter with a mechanically heated catheter tip having a grooved friction producing plug.

FIG. 4 illustrates a cross sectional view (perpendicular to the longitudinal axis of the catheter) of a fourth catheter with a mechanically heated catheter tip 400. The fourth catheter tip 400, as illustrated in FIGS. 4A and 4B can include a friction producing plug 130' a drive wire 140', a thermally conductive catheter tip 170' constructed out of catheter high friction material 160', at least one aligning ridge 410, and/or at least one aligning trench 420. In operation, the fourth catheter tip 400 can operate in substantially the same manner as the catheter with a mechanically heated catheter tip 100 of FIG. 1. In some embodiments, the aligning ridge(s) 410 and the aligning trench(s) 420 of the fourth catheter tip 400 can prevent substantially all rotation about the longitudinal axis of the catheter. In some embodiments, the fourth catheter tip 400 permits primarily only axial oscillation of the friction producing plug 130'.

In some embodiments, the thermally conductive catheter tip 170' can include one or more aligning ridges 410 and the friction producing plug 130' can include the same number of aligning trenches 420. In these embodiments, the aligning ridges 410 of the thermally conductive catheter tip 170' fit into the aligning trenches 420 of the friction producing plug 130' allowing the friction producing plug 130' to ride axially along the aligning ridges 410 during oscillation.

In some embodiments, there can be only one aligning ridge 410. In other embodiments, there can be multiple aligning ridges 410 in the range of about 2-6 ridges, and about 2-4 ridges, including 3 ridges or any other number of ridges which guides the friction producing plug 130' upon axial oscillation. In some embodiments, the aligning ridges 410 may be constructed out of catheter high friction material 160' as shown in FIG. 4A. In other embodiments, the aligning ridges 410 may be constructed out of a low friction material as shown in FIG. 4B.

In some embodiments, there can be only one aligning trench 420. In other embodiments, there can be multiple aligning trenches 420 in the range of about 2-6 trenches, and about 2-4 trenches, including 3 trenches or an other number of trenches which guides the friction producing plug 130' upon axial oscillation. In some embodiments, the entire friction producing plug 130', and therefore the entire surface of the aligning trenches 420, is constructed out of a high friction material (as shown in FIG. 4A). In other embodiments, the friction producing plug 130' is constructed out of at least two separate materials (as disclosed in the discussion of FIG. 2). In such embodiments, substantially the entire surface of the aligning trenches 420 can be constructed out of a material distinct from the high friction coating 230' (e.g., a low friction material), as shown in FIG. 4B.

In some embodiments, the fourth catheter tip 400 which includes at least one aligning ridge 410 and at least one aligning trench 420 can include a plug stop 340 as discussed with respect to FIG. 3.

FIG. 5 illustrates a fifth catheter with a targeted mechanically heated catheter tip 500. The fifth catheter tip 500 includes a catheter body 110', a thermally conductive catheter tip 170' constructed out of both catheter high friction material 160' and catheter thermally insulating material 510, a catheter tip distal end 120', a friction producing plug 130', and a drive wire 140'. In operation, the fifth catheter tip 500 operates in a manner substantially the same as the catheter with a mechanically heated catheter tip 100 of FIG. 1.

Figure 5A:
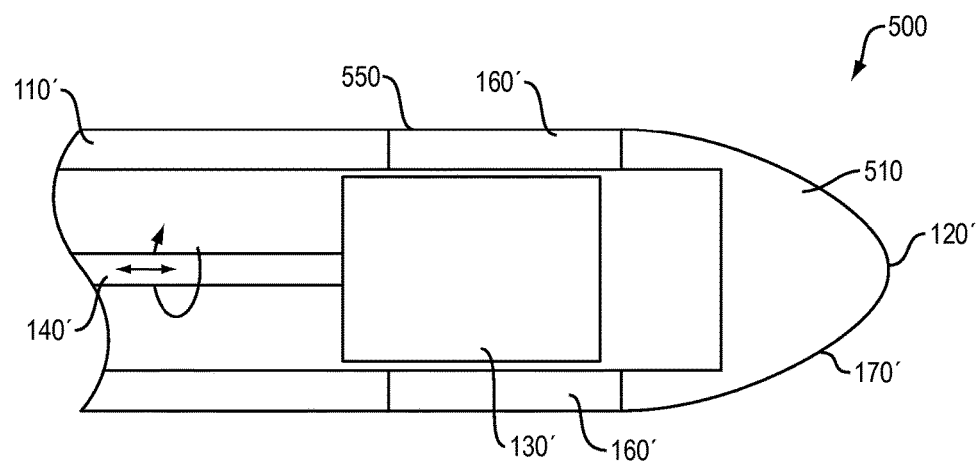
FIG. 5A illustrates a longitudinal section view of one embodiment of a catheter with a mechanically heated catheter tip having a windowed tip.

In some embodiments, as illustrated in FIG. 5A, the thermally conductive catheter tip 170' of the fifth catheter tip 500 includes a window 550 of catheter high friction material 160'. In these embodiments, the bulk of the thermally conductive catheter tip 170' (excluding the window 550 of catheter high friction material 160') can be constructed out of catheter thermally insulating material 510. In some embodiments, the window 550 will produce and conduct heat thereby advantageously permitting enhanced targeting of the thermal energy generated by the friction producing plug 130'. The window 550 can be any shape desired and can be located anywhere practicable on the thermally conductive catheter tip 170'. For example, the window 550 can be a single concentric band around the entirety of the thermally conductive catheter tip 170' as shown in FIG. 5A. Alternatively, the window 550 can be a single circle on only one side of the thermally conductive catheter tip 170' (not shown). Representative examples of catheter thermally insulating material 510 appropriate for forming on or with the thermally conductive catheter tip 170', as illustrated in FIG. 5A, include, but are not limited to, polymers (e.g., polytetrafluoroethylene, polyethylene, etc.), rubber, and polycarbonate, or any other biocompatible thermal insulator.

Figure 5B:
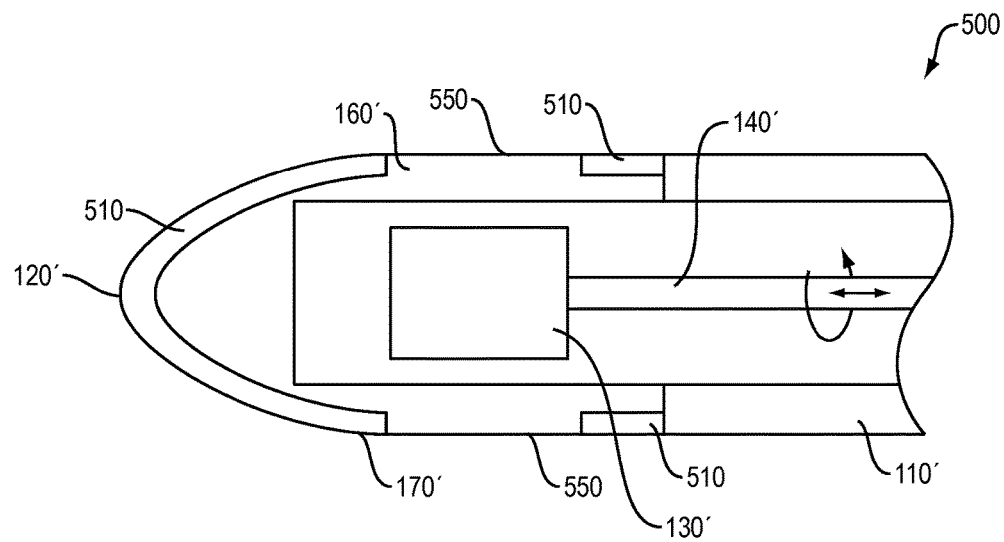
FIG. 5B illustrates a longitudinal section view of another embodiment of another catheter with a mechanically heated catheter tip having a windowed tip.

In some embodiments, as illustrated in FIG. 5B, the thermally conductive capacitor tip 170' of the fifth catheter tip 500 is constructed monolithically out of catheter high friction material 160' then selectively coded in catheter thermally insulating material 510 to produce the window 550. The coating of catheter thermally insulating material 510 can be inlay, an onlay, or any other type of coating that allows selective exposure of the catheter high friction material 160'. In some embodiments, only the window 550 not covered by the catheter thermally isolating material will allow the conductance of heat, thereby advantageously permitting enhanced targeting of the thermal energy generated by the friction producing plug 130'. The use of a coating of catheter thermally insulating material 510 as illustrated in FIG. 5B can permit more detailed patterns of windows 550 than the constructed in FIG. 5A thereby advantageously allowing a great degree of targeting of the heat produced by the fifth catheter tip 500. Representative examples of catheter thermally insulating material 510 appropriate for coding thermally conductive catheter tip 170' as illustrated in FIG. 5B include, but are not limited to, polymers (e.g., polytetrafluoroethylene, polyethylene, etc.), rubber, and polycarbonate, or any other biocompatible thermal insulator.

Figure 6A:
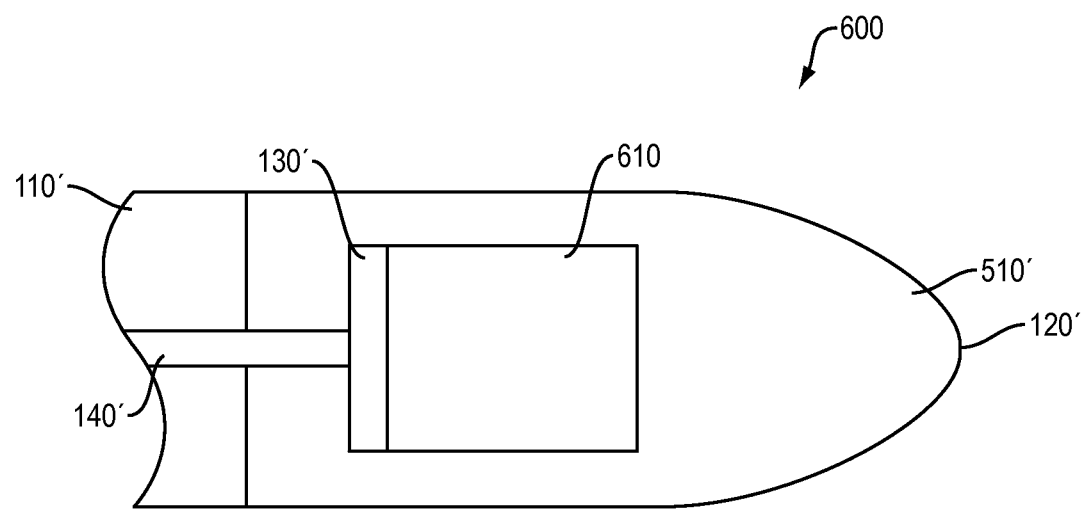
FIG. 6A illustrates a longitudinal section view of another embodiment of another catheter with a mechanically heated catheter tip having a windowed tip.
Figure 6B:
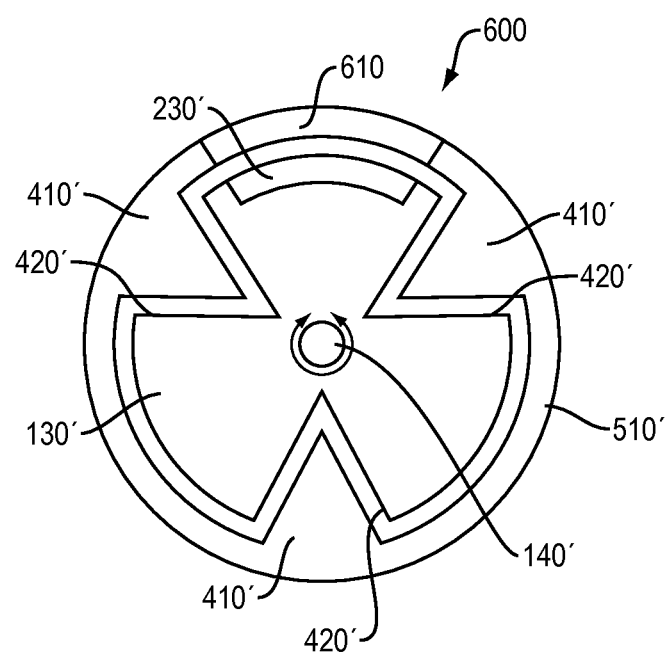
FIG. 6B illustrates a section view perpendicular to the longitudinal axis of the embodiment of another catheter with a mechanically heated catheter tip having a windowed tip shown in FIG. 6A.

FIG. 6A and FIG. 6B illustrate a sixth catheter with a targeted mechanically heated catheter tip 600. The sixth catheter tip 600 includes a catheter body 110', a friction producing plug 130', a drive wire 140', a catheter tip distal end 120', a catheter thermally insulating material 510', at least one aligning ridge 410', at least one aligning trench 420', catheter thermally insulating material 510', high friction coating 230', and a high friction window 610. In operation, the sixth catheter tip operates in a manner substantially the same as the fourth catheter with a mechanically heated catheter tip 400 of FIG. 4. The sixth catheter tip 600 combines the aligning ridges 410' and the high friction coating 230' to permanently align the high friction coating 230' on the friction producing plug 130' with the external high friction window 610 (similar to the window 550 of FIG. 5). The various embodiments discussed in the previous figures, notably FIG. 2, FIG. 4, and FIG. 5 can also be applied to FIG. 6A and FIG. 6B.

In some embodiments, it is contemplated that a heat conductive gel may be placed in the treatment region or airway before the probe is placed to administer treatment. The heat conductive gel may conduct heat away from the probe into the target tissue more efficiently than air. Some examples of heat conductive gel include saline absorbing gel, saline gel, sodium polyacrylate, acrylic acid crosslinked sodium salt, polyacrylic acid crosslinked sodium salt such as Waste Lock brand super absorbent 770 manufactured by M2 Polymer, water based gel lubricant such as Femglide used on catheters and equipment, or the like.

The systems for mechanically heated catheters disclosed herein can provide for an improved catheter for thermal application because, for example, it provides thermal energy directly without the need for any electricity in the body. The mechanically heated catheters may not require the complicated electrical systems that other thermal catheter systems often require to heat tissues as they are purely mechanical—rather, they can create heat directly which can be directly conducted or convected into the target tissue site.

Of course, the foregoing description is of certain features, aspects and advantages of the present disclosure, to which various changes and modifications can be made without departing from the spirit and scope of the present disclosure. Thus, for example, those of skill in the art will recognize that the disclosure can be embodied or carried out in a manner that achieves or optimizes one advantage or a group of advantages as taught herein without necessarily achieving other objects or advantages as can be taught or suggested herein. In addition, while a number of variations of the disclosure have been shown and described in detail, other modifications and methods of use, which are within the scope of this disclosure, will be readily apparent to those of skill in the art based upon this disclosure. It is contemplated that various combinations or sub-combinations of the specific features and aspects between and among the different embodiments can be made and still fall within the scope of the disclosure. Accordingly, it should be understood that various features and aspects of the disclosed embodiments can be combined with or substituted for one another in order to form varying modes of the discussed devices, systems and methods (e.g., by excluding features or steps from certain embodiments, or adding features or steps from one embodiment of a system or method to another embodiment of a system or method).

What is claimed is:

1. A catheter to deliver heat, comprising:
   a catheter body comprising an axial lumen having a length extending from a proximal end to a distal end;
   a hollow catheter tip, wherein the hollow catheter tip is operably connected to the distal end of the axial lumen of the catheter body;
   a friction producing plug, wherein the friction producing plug is disposed within the hollow catheter tip, and wherein at least a portion of the friction producing plug is frictionally coupled to at least a portion of an interior wall of the hollow catheter tip;
   a drive wire having a proximal end and a distal end and extending through the length of the axial lumen of the catheter body and into the hollow catheter tip, and wherein the distal end of the drive wire is configured to directly attach to the friction producing plug; and
   a power source,
      wherein the power source is configured to attach to the proximal end of the drive wire, and
      wherein the hollow catheter tip contains thermally conductive material,
      wherein movement of the drive wire causes a corresponding motion of the friction producing plug, thereby producing heat as a result of friction between the friction producing plug and the interior wall of the hollow catheter tip,
      wherein the produced heat provides heat to tissue surrounding the hollow catheter tip thereby heat treating the tissue,
   wherein the catheter body comprises a plug stop within the axial lumen and proximal from the hollow catheter tip.

2. The catheter of claim 1, wherein the power source is configured to provide rotational movement to the drive wire.

3. The catheter of claim 1, wherein the power source is configured to provide axial translational movement to the drive wire.

4. The catheter of claim 1, wherein movement of the drive wire is modulated using a power input selected from the group including: electric motors, ultrasonic horns, piezoelectric devices, mechanical air driven devices, harmonic devices, air driven pistons, solenoids, and electromagnet drivers.

5. The catheter of claim 1, wherein the hollow catheter tip is filled with oil.

6. The catheter of claim 1, wherein the hollow catheter tip is constructed out of at least one material selected from the group including: stainless steel, titanium, and nitinol.

7. The catheter of claim 1, wherein the friction producing plug is constructed out of at least one material selected from the group including: ceramic, copper, steel, minerals, cellulose, aramid, chopped glass, rubber and brass, and polyether ether ketone.

8. The catheter of claim 7, wherein the friction producing plug is formed monolithically out of a single material.

9. The catheter of claim 8, wherein the friction producing plug is formed in a shape selected from the group consisting of spherical, cylindrical, and bullet shaped.

10. The catheter of claim 1, wherein a shape of the plug stop is selected from a group consisting of continuous flange-style and bullet shaped.

11. The catheter of claim 1, wherein the catheter tip is coated in thermally insulating material and a heat conductive gel is placed in a treatment region before a treatment is applied.

* * * * *